United States Patent
Grennberg et al.

(10) Patent No.: US 8,200,338 B2
(45) Date of Patent: Jun. 12, 2012

(54) FLEXIBLE CIRCUIT ELECTRODE ARRAY FOR IMPROVED LAYER ADHESION

(75) Inventors: Robert Jay Grennberg, Los Angeles, CA (US); Mark S. Humayun, Glendale, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 522 days.

(21) Appl. No.: 11/331,625

(22) Filed: Jan. 13, 2006

(65) Prior Publication Data

US 2006/0190058 A1     Aug. 24, 2006

Related U.S. Application Data

(62) Division of application No. 11/293,400, filed on Dec. 1, 2005, now Pat. No. 8,068,913.

(60) Provisional application No. 60/633,190, filed on Dec. 3, 2004.

(51) Int. Cl.
 *A61N 1/18* (2006.01)
(52) U.S. Cl. ............ 607/53; 607/54; 607/116; 607/152
(58) Field of Classification Search .............. 600/26, 600/27, 372–397; 607/53, 54, 116, 141, 607/152

See application file for complete search history.

(56) References Cited

U.S. PATENT DOCUMENTS

| | | | |
|---|---|---|---|
| 3,699,970 A | 10/1972 | Brindley et al. | |
| 4,018,218 A * | 4/1977 | Carlson et al. | 600/26 |
| 4,487,652 A | 12/1984 | Almgren | |
| 4,539,995 A * | 9/1985 | Segawa | 600/385 |
| 4,573,481 A | 3/1986 | Bullara | |
| 4,628,933 A | 12/1986 | Michelson | |
| 4,837,049 A | 6/1989 | Byers et al. | |
| 4,979,508 A * | 12/1990 | Beck | 607/54 |
| 4,996,629 A | 2/1991 | Christiansen et al. | |
| 5,108,819 A | 4/1992 | Heller et al. | |
| 5,109,844 A | 5/1992 | de Juan, Jr. et al. | |
| 5,169,380 A * | 12/1992 | Brennan | 600/26 |
| 5,178,957 A | 1/1993 | Kolpe et al. | |
| 5,215,088 A | 6/1993 | Normann et al. | |
| 5,324,322 A * | 6/1994 | Grill et al. | 607/118 |
| 5,505,201 A * | 4/1996 | Grill et al. | 600/371 |
| 5,935,155 A | 8/1999 | Humayun et al. | |
| 5,987,361 A * | 11/1999 | Mortimer | 607/118 |
| 6,071,819 A | 6/2000 | Tai et al. | |
| 6,235,046 B1 * | 5/2001 | Gerdt | 607/88 |
| 6,324,429 B1 | 11/2001 | Shire et al. | |
| 6,374,143 B1 | 4/2002 | Berrang et al. | |
| 6,847,847 B2 | 1/2005 | Nisch et al. | |
| 2001/0037061 A1 | 11/2001 | Eckmiller et al. | |
| 2002/0091421 A1 * | 7/2002 | Greenberg et al. | 607/54 |
| 2003/0097166 A1 * | 5/2003 | Krulevitch et al. | 607/116 |
| 2003/0158588 A1 | 8/2003 | Rizzo et al. | |
| 2003/0192784 A1 * | 10/2003 | Zhou | 205/109 |

(Continued)

*Primary Examiner* — Carl H Layno
*Assistant Examiner* — Jennifer Ghand
(74) *Attorney, Agent, or Firm* — Scott B. Dunbar; Alessandro Steinfl

(57) ABSTRACT

Present invention is a method of improving circadian rhythms in blind people by stimulation the visual neural system. Ideally a retinal prosthesis of the type used to restore vision can be used to restore normal circadian rhythms. Additionally, brightness on the prosthesis can be increased in the morning and decreased in the evening to stimulate normal Circadian rhythms. Alternatively, if a retinal prosthesis is not preferable, the retina can be stimulated externally, during the day and not at night. While such eternal stimulation can not produced artificial vision, it can stimulate normal circadian rhythms.

18 Claims, 10 Drawing Sheets

U.S. PATENT DOCUMENTS

| | | | |
|---|---|---|---|
| 2004/0121528 A1* | 6/2004 | Krulevitch et al. | 438/166 |
| 2004/0210122 A1* | 10/2004 | Sieburg | 600/393 |
| 2004/0220652 A1* | 11/2004 | Zhou et al. | 607/141 |
| 2006/0003090 A1* | 1/2006 | Rodger et al. | 427/96.1 |
| 2006/0069416 A1* | 3/2006 | Nisch et al. | 607/54 |
| 2007/0169333 A1* | 7/2007 | Donoghue et al. | 29/592 |

* cited by examiner

FLEXIBLE CIRCUIT ELECTRODE ARRAY FOR IMPROVED LAYER ADHESION

CROSS-REFERENCE TO RELATED APPLICATIONS

This application is a divisional of U.S. patent application Ser. No. 11/293,400, "Visual Prosthesis for Improved Circadian Rhythms and Method of Improving the Circadian Rhythms", filed Dec. 1, 2005 now U.S. Pat. No. 8,068,913 issued Nov. 29, 2011, the disclosure of which is incorporated herein by reference, and which claims the benefit of U.S. Provisional Application No. 60/633,190 "Visual Prosthesis for Improved Circadian Rhythms", filed Dec. 3, 2004, the disclosure of which is incorporated herein by reference.

STATEMENT REGARDING FEDERALLY SPONSORED RESEARCH OR DEVELOPMENT

This invention was made with government support under grant No. R24EY12893-01, which has been awarded by the National Institutes of Health. The government has certain rights in the invention.

BACKGROUND OF THE INVENTION

1. Field of the Invention

The present invention is generally directed to neural stimulation and more specifically to neural stimulation of the visual system for improved circadian rhythms and a method of improving the circadian rhythms.

2. Background of the Invention

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretial). This placement must be mechanically stable, minimize the distance between the device electrodes and the visual neurons, and avoid undue compression of the visual neurons.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 µA current resulted in visual cortical responses. These experiments were carried out with needle-shaped electrodes that penetrated the surface of the retina (see also U.S. Pat. No. 4,628,933 to Michelson).

In U.S. Pat. No. 3,699,970 "Striate Cortex Stimulator" to Giles Skey Brindley et al. an implantable device is disclosed comprising a plurality of electrodes for stimulating the striate cortex.

In U.S. Pat. No. 4,487,652 "Slope. Etch of Polyimide" to Carl W. Amgren a semiconductor having an insulating layer overlying a metal layer is disclosed, wherein the insulator comprises an upper oxide layer, an intermediate polyimide layer, and a lower oxide layer in contact with the metal layer, a method for etching a via from an upper surface of the polyimide layer to the metal layer comprising the steps of applying photoresist; etching an opening from an upper surface of the photoresist layer to the upper oxide layer at a location for forming the via so that an upper surface of the upper oxide layer is exposed at the via location; heating the photoresist to cause a more gradual slope of the photoresist layer from the upper surface of the upper oxide layer at the via location to the upper surface of the photoresist layer; applying reactive ion etchant with a predetermined selectivity between photoresist and oxide to transfer the slope of the photoresist layer to the upper oxide layer at a predetermined ratio; and applying a reactive ion etchant with a predetermined selectivity between oxide and polyimide to transfer the slope of the upper oxide layer to the polyimide layer at a predetermined ratio, whereby the lower oxide layer is simultaneously etched to expose the metal layer at the via location.

In U.S. Pat. No. 4,573,481 "Implantable Electrode Array" to Leo A. Bullara an electrode assembly for surgical implantation on a nerve of the peripheral nerve system is disclosed.

In U.S. Pat. No. 4,628,933 "Method and Apparatus for Visual Prosthesis" to Robin P. Michelson a visual prosthesis for implantation in the eye in the optical pathway thereof is disclosed.

In U.S. Pat. No. 4,837,049 "Method of Making an Electrode Array" to Charles L. Byers et al. a very small electrode array which penetrates nerves for sensing electrical activity therein or to provide electrical stimulation is disclosed.

In U.S. Pat. No. 4,996,629 "Circuit Board with Self-Supporting Connection Between Sides" to Robert A. Christiansen et al. a copper supporting sheet is disclosed having vias for connecting semiconductor chips to surface mount components. A laminate of polyimide has vias corresponding to the supporting layer vias with copper covering those vias.

In U.S. Pat. No. 5,108,819 "Thin Film Electrical Component" to James W. Heller a thin film electrical component is disclosed comprising a rigid glass carrier plate, a substrate bonded to the rigid glass carrier plate, the substrate comprising a polyimide establishing a bond with the rigid glass carrier plate that is broken upon immersion of the substrate and the rigid glass carrier plate in one of a hot water bath and a warm temperature physiologic saline bath to release the polymer from attachment to the rigid glass carrier plate, and means for providing an electrical circuit, the providing means being bonded to the substrate and undisrupted during release of the substrate from attachment to the rigid glass carrier plate.

In U.S. Pat. No. 5,109,844 "Retinal Microstimulation" to Eugene. de Juan Jr. et al. a method for stimulating a retinal ganglion cell in a retina without penetrating the retinal basement membrane at the surface of the retina is disclosed.

In U.S. Pat. No. 5,178,957 "Noble Metal-Polymer Composites and Flexible Thin-Film Conductors Prepared Therefrom" to Vasant V. Kolpe a composite article is disclosed comprising a polymeric support selected from the group consisting of a polyimide, polyethylene terephthalate, and polyester-ether block copolymer having a noble metal deposited directly onto at least one surface, wherein said deposited metal exhibits a peel force of at least about 0.05 kg per millimeter width after 24 hour boiling saline treatment.

In U.S. Pat. No. 5,215,088 "Three-Dimensional Electrode Device" to Richard A. Norman et al. a three-dimensional electrode device for placing electrodes in close proximity to cell lying at least about 1000 microns below a tissue surface is disclosed.

In U.S. Pat. No. 5,935,155 "Visual Prosthesis and Method of Using Same" to Mark S. Humayun et al. a visual prosthesis is disclosed comprising a camera for receiving a visual image and generating a visual signal output, retinal tissue stimulation circuitry adapted to be operatively attached to the user's retina, and wireless communication circuitry for transmitting the visual signal output to the retinal tissue stimulation circuitry within the eye.

In U.S. Pat. No. 6,071,819 "Flexible Skin Incorporating MEMS Technology" to Yu-Chong Tai a method of manufacturing a flexible microelectronic device is disclosed comprising first etching a lower side of a wafer using a first caustic agent; depositing a first layer of aluminum on an upper side of the wafer; patterning the first layer of aluminum; depositing a first layer of polyimide on the upper side of the wafer, covering the first layer of aluminum; depositing a second layer of aluminum on the upper side of the wafer, covering the first layer of polyimide; depositing a second layer of polyimide on the upper side of the wafer, covering the second layer of aluminum; depositing a third layer of aluminum on the lower side of the wafer; patterning the third layer of aluminum; second etching the lower side of the wafer using the third layer of aluminum as a mask and the first layer of aluminum as an etch stop and using a less caustic agent than said first caustic agent, such that the wafer is divided into islands with gaps surrounding each island; and depositing a third layer of polyimide on the lower side of the wafer, such that the gaps are at least partially filled.

In U.S. Pat. No. 6,324,429 "Chronically Implantable Retinal Prosthesis" to Doug Shire et al. an apparatus is disclosed which is in contact with the inner surface of the retina and electrically stimulates at least a portion of the surface of the retina.

In U.S. Pat. No. 6,374,143 "Modiolar Hugging Electrode Array" to Peter G. Berrang et al. a cochlear electrode array for stimulating auditory processes is disclosed.

In U.S. Pat. No. 6,847,847 "Retina Implant Assembly and Methods for Manufacturing the Same" to Wilfried Nisch et al. a retina implant is disclosed comprising a chip in subretinal contact with the retina and a receiver coil for inductively coupling there into electromagnetic energy.

In U.S. patent application Ser. No. 20010037061 A1, "Microcontact structure for neuroprostheses for implantation on nerve tissue and method therefore" to Rolf Eckmiller et al. a four layer microcontact structure is disclosed in which the active connection between the microcontact structure and the nerve tissue is brought about by electrical stimulation. The layer adjacent to the nerve tissue to be stimulated is composed of the polymer polyimide and contains penetrating electrodes made of platinum which forms the adjoining layer. There follows a further layer of the polyimide and a layer of the polymer polyurethane. Polyurethane has the property of thermal expansion relative to polyimide.

In U.S. patent application Ser. No. 2003/0158588 A1 "Minimal Invasive Retinal Prosthesis" to John F. Rizzo et al. a retinal prosthesis is disclosed comprising an RF coil attached to the outside of and moving with an eye to receive power from an external power source; electronic circuitry attached to and moving with the eye and electrically connected to the RF coil; a light sensitive array electrically connected to the electronic circuitry and located within the eye for receiving incident light and for generating an electrical signal in response to the incident light; and a stimulating array abutting a retina of the eye and electrically connected to the electronic circuitry to stimulate retinal tissue in response to the electrical signal from the light sensitive array. A supporting silicone substrate has a polyimide layer spun onto its surface and cured. The copper or chrome/gold conducting layer is then added and patterned using wet chemical etching or a photoresist lift-off process. Next, a second polyimide layer is spun on, and the regions where circuit components are to be added are exposed by selective dry etching or laser ablation of the upper polyimide layer in the desired areas. Finally, the completed components are removed from their supporting substrate.

Eugene de Juan Jr. et al. at Duke University Eye Center inserted retinal tacks into retinas in an effort to reattach retinas that had detached from the underlying choroid, which is the source of blood supply for the outer retina and thus the photoreceptors. See for example E. de Juan Jr., et al., "Retinal tacks", Am J Ophthalmol. 1985 Mar. 15; 99 (3):272-4.

Hansjoerg Beutel et al. at the Fraunhofer Institute for Biomedical Engineering IBMT demonstrated the bonding of a gold ball by force, temperature, and ultrasound onto an aluminum metal layer. See for example Hansjoerg Beutel, Thomas Stieglitz, Joerg-Uwe Meyer: "Versatile Microflex-Based Interconnection Technique," Proc. SPIE Conf. on Smart Electronics and MEMS, San Diego, Calif., March 1998, vol. 3328, pp 174-182. A robust bond can be achieved in this way. However, encapsulation proves difficult to effectively implement with this method. Gold, while biocompatible, is not completely stable under the conditions present in an implant device since it dissolves by electromigration when implanted in living tissue and subject to an electric current. See for example Marcel Pourbaix: "Atlas of Electrochemical Equilibria in Aqueous Solutions", National Association of Corrosion Engineers, Houston, 1974, pp 399-405.

A system for retinal stimulation comprising a polyimide-based electrodes being coated with platinum black are described by Andreas Schneider and Thomas Stieglitz. See for example Andreas Schneider, Thomas Stieglitz: "Implantable Flexible Electrodes for Functional Electrical Stimulation", Medical Device Technology, 2004.

It is known that circadian rhythms drive our body's natural cycles of wake and sleep. The hormone melatonin is produced in increasing quantities in the evening and lesser quantities in the morning. Blind people generally do not have normal circadian rhythms and do not produced extra melatonin in the evening. Hence, the perception of light, at least in part, drives the circadian rhythm and the production of melatonin.

SUMMARY OF THE INVENTION

Present invention is a method of improving circadian rhythms in blind people by stimulation the visual neural system. Ideally a retinal prosthesis of the type used to restore vision can be used to restore normal circadian rhythms. Additionally, brightness on the prosthesis can be increased in the morning and decreased in the evening to stimulate normal circadian rhythms. Alternatively, if a retinal prosthesis is not preferable, the retinal can be stimulated externally, during the day and not at night. While such eternal stimulation can not produced artificial vision, it can stimulate normal circadian rhythms.

One aspect of the present invention is a visual prosthesis for stimulating circadian rhythms comprising at least one electrode suitable for electrically stimulating visual neurons;
an electrical driver for applying a controlled electrical potential on said electrode; and
a timer for controlling activation of said electrical driver.

Another aspect of the present invention is a flexible circuit electrode array for improving circadian rhythms, comprising an insulating polymer layer;
at least one trace containing a base conducting layer, an intermediate conducting layer and a top conducting layer, embedded in said insulating polymer layer; and
at least one electrode connected to said conducting layer of said trace through a via in said insulating polymer layer and said top coat layer.

Another aspect of the intention is a method of using a flexible circuit electrode array for manufacturing a visual prosthesis for increasing the melatonin levels at night.

DETAILED DESCRIPTION OF THE INVENTION

Figure 1:
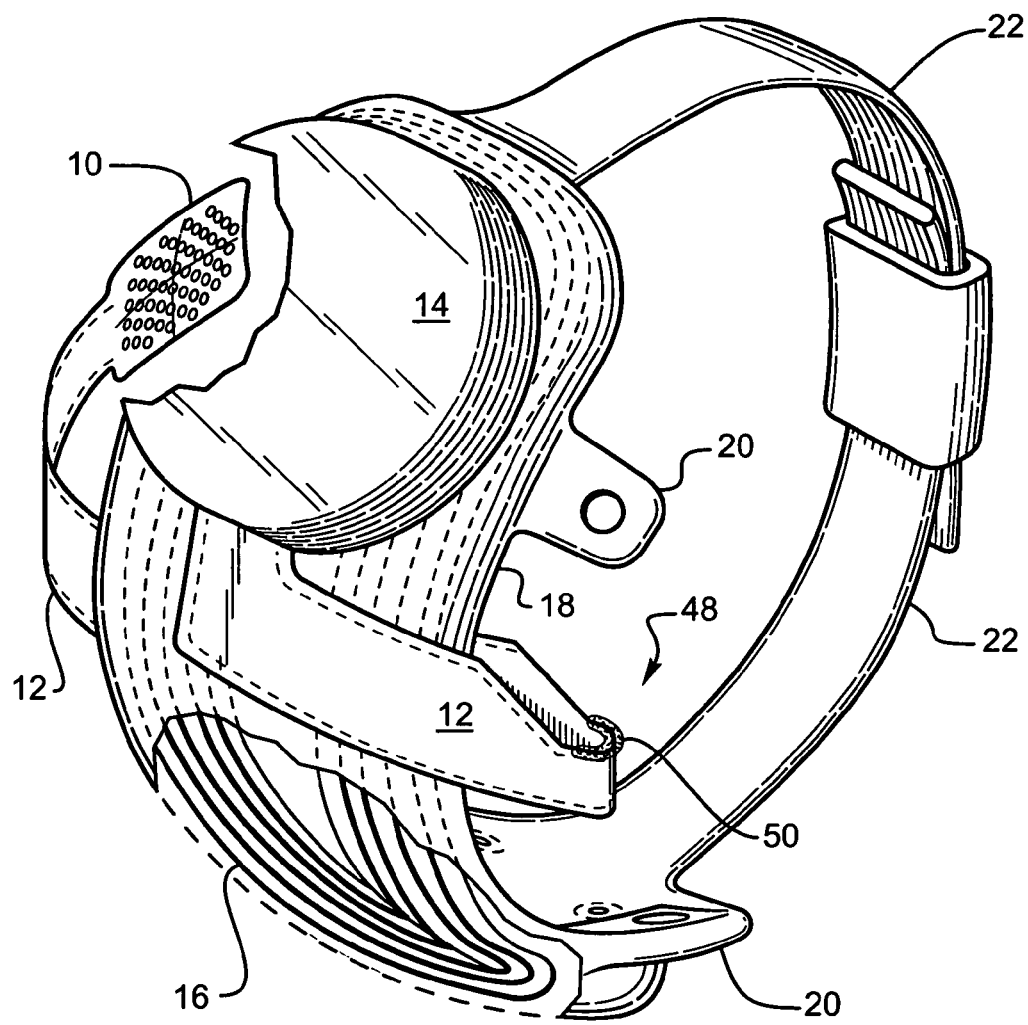
FIG. 1 depicts a perspective view of the implanted portion of the preferred retinal prosthesis including a twist in the array to reduce the width of a scleratomy and a sleeve to promote sealing of the scleratomy.

FIG. 1 shows a perspective view of the implanted portion of the preferred retinal prosthesis. A flexible circuit electrode array 10 is mounted by a retinal tack or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by a molded body 18. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil 16.

The implanted portion of the retinal prosthesis may include the additional feature of a gentle twist or fold 48 in the flexible circuit cable 12, where the flexible circuit cable 12 passes through the sclera (scleratomy). The twist 48 may be a simple sharp twist, or fold; or it may be a longer twist, forming a tube. While the tube is rounder, it reduces the flexibility of the flexible circuit cable 12. A simple fold reduces the width of the flexible circuit cable 12 with only minimal impact on flexibility.

Further, silicone or other pliable substance may be used to fill the center of the tube or fold 48 formed by the twisted flexible circuit cable 12. Further it is advantageous to provide a sleeve or coating 50 that promotes healing of the scleratomy. Polymers such as polyimide, which may be used to form the flexible circuit cable 12 and flexible circuit electrode array 10, are generally very smooth and do not promote a good bond between the flexible circuit cable 12 and scleral tissue. A sleeve or coating 50 of polyester, collagen, silicone, Gore-Tex® or similar material would bond with scleral tissue and promote healing. In particular, a porous material will allow scleral tissue to grow into the pores promoting a good bond.

The entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package 14 in an area of fatty tissue between the rectus muscles, eye motion does not cause any flexing which might fatigue, and eventually damage, the device.

Human vision provides a field of view that is wider than it is high. This is partially due to fact that we have two eyes, but even a single eye provides a field of view that is approximately 90° high and 140° to 160° degrees wide. It is therefore, advantageous to provide a flexible circuit electrode array 10 that is wider than it is tall. This is equally applicable to a cortical visual array. In which case, the wider dimension is not horizontal on the visual cortex, but corresponds to horizontal in the visual scene.

Figure 2:
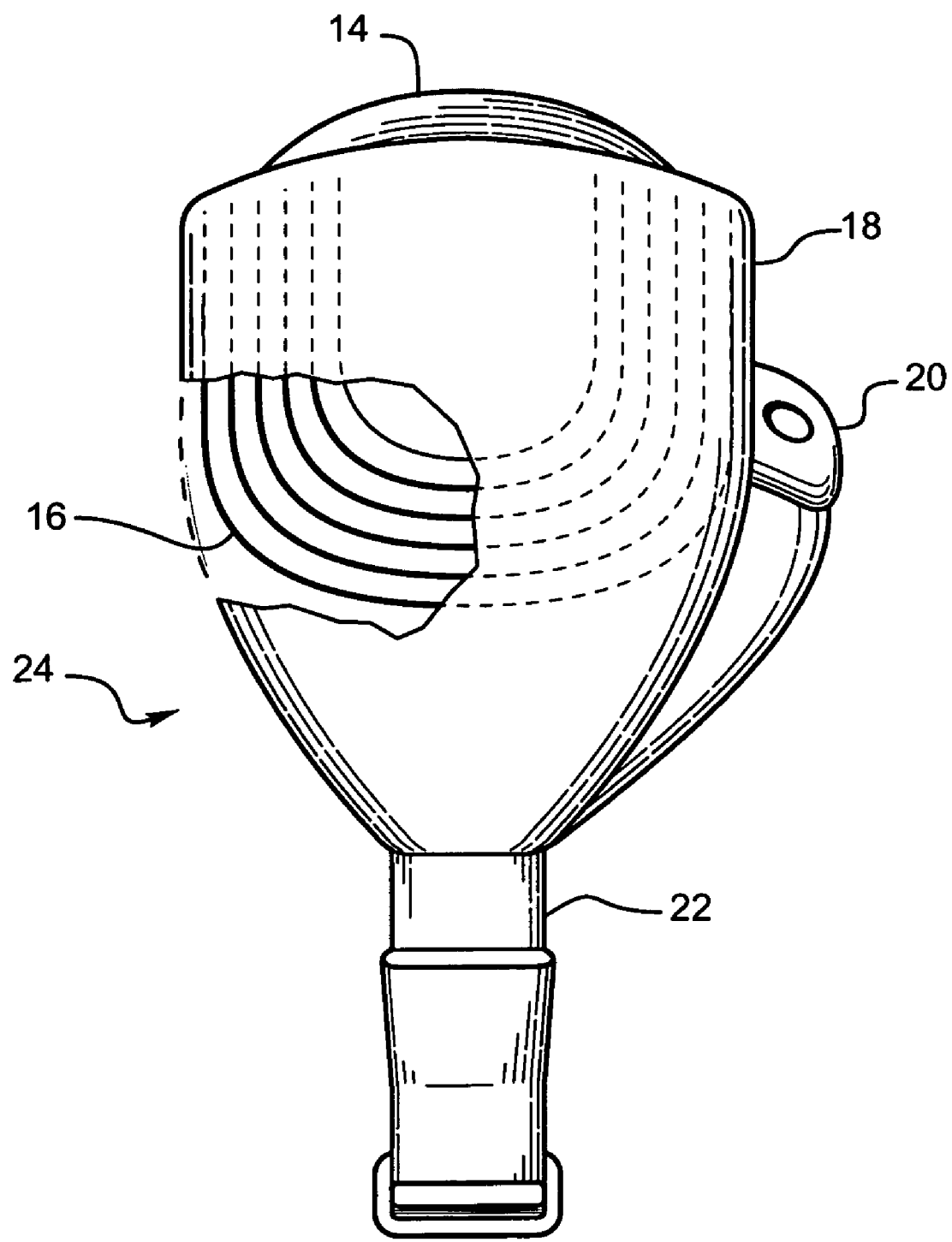
FIG. 2 depicts a perspective view of the implanted portion of the retinal prosthesis showing the fan tail in more detail.
Figure 3A:
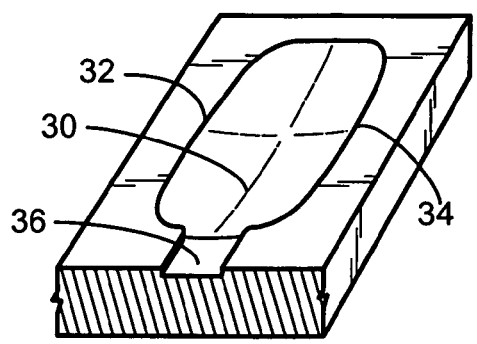
FIGS. 3a-3e depicts a perspective view of molds for forming the flexible circuit array in a curve.
Figure 3B:
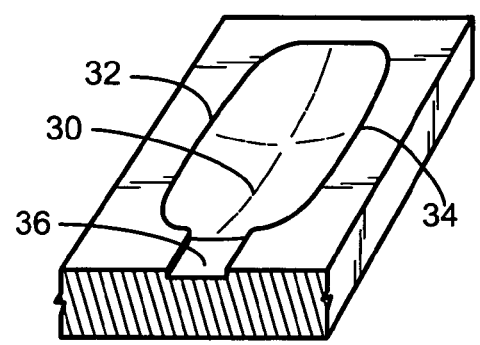
Figure 3C:
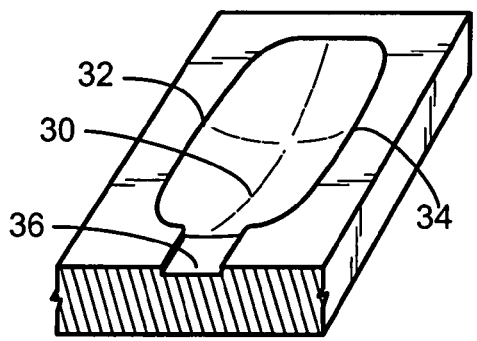
Figure 3D:
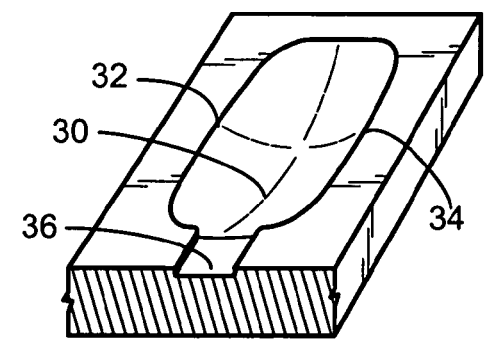
Figure 3E:
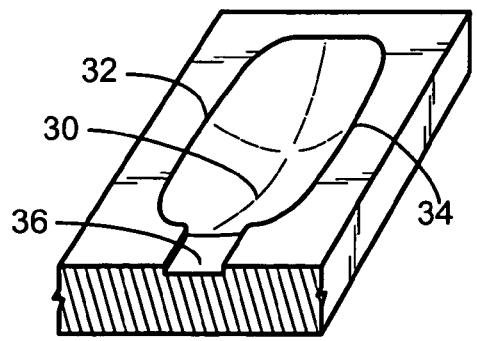

FIG. 2 shows a side view of the implanted portion of the retinal prosthesis, in particular, emphasizing the fan tail 24. When implanting the retinal prosthesis, it is necessary to pass the strap 22 under the eye muscles to surround the sclera. The secondary inductive coil 16 and molded body 18 must also follow the strap 22 under the lateral rectus muscle on the side of the sclera. The implanted portion of the retinal prosthesis is very delicate. It is easy to tear the molded body 18 or break wires in the secondary inductive coil 16. In order to allow the molded body 18 to slide smoothly under the lateral rectus muscle, the molded body 18 is shaped in the form of a fan tail 24 on the end opposite the electronics package 14.

The flexible circuit electrode array 10 is a made by the following process. First, a layer of polymer is applied to a supporting substrate (not part of the array) such as glass. The polymer layer or films of the present invention can be made, for example, any one of the various polyfluorocarbons, polyethylene, polypropylene, polyimide, polyamide, silicone or other biologically inert organic polymers. Layers may be applied by spinning, meniscus coating, casting, sputtering or other physical or chemical vapor deposition, or similar process. Subsequently, a metal layer is applied to the polymer. The metal is patterned by photolithographic process. Preferably, a photoresist is applied and patterned by photolithography followed by a wet etch of the unprotected metal. Alternatively, the metal can be patterned by lift-off technique, laser ablation or direct write techniques.

It is advantageous to make the metal thicker at the electrode and bond pad to improve electrical continuity. This can be accomplished through any of the above methods or electroplating. Then, the top layer of polymer is applied over the metal. Openings in the top layer for electrical contact to the electronics package 14 and the flexible circuit electrode array 10 may be accomplished by laser ablation or reactive ion etching (RIE) or photolithograph and wet etch. Making the electrode openings in the top layer smaller than the electrodes promotes adhesion by avoiding delaminating around the electrode edges.

The pressure applied against the retina by the flexible circuit electrode array 10 is critical. Too little pressure causes increased electrical resistance between the array and retina. Common flexible circuit fabrication techniques such as photolithography generally require that a flexible circuit electrode array 10 be made flat. Since the retina is spherical, a flat array will necessarily apply more pressure near its edges, than at its center. With most polymers, it is possible to curve them when heated in a mold. By applying the right amount of heat to a completed array, a curve can be induced that matches the curve of the retina. To minimize warping, it is often advantageous to repeatedly heat the flexible circuit in multiple molds, each with a decreasing radius. FIG. 3 illustrates a series of molds according to the preferred embodiment. Since the flexible circuit will maintain a constant length, the curvature 30 must be slowly increased along that length. As the curvature 30 increases in successive molds (FIGS. 3a-3e) the straight line length between ends 32 and 34, must decrease to keep the length along the curvature 30 constant, where mold 3E approximates the curvature 30 of the retina or other desired neural tissue. The molds provide a further opening 36 for the flexible circuit cable 12 of the array to exit the mold without excessive curvature.

It should be noted that suitable polymers include thermoplastic materials and thermoset materials. While a thermoplastic material will provide some stretch when heated a thermoset material will not. The successive molds are, therefore, advantageous only with a thermoplastic material. A thermoset material works as well in a single mold as it will with successive smaller molds. It should be noted that, particularly with a thermoset material, excessive curvature 30 in three dimensions will cause the polymer material to wrinkle at the edges. This can cause damage to both the array and the retina. Hence, the amount of curvature 30 is a compromise between the desired curvature, array surface area, and the properties of the material.

Figure 4:
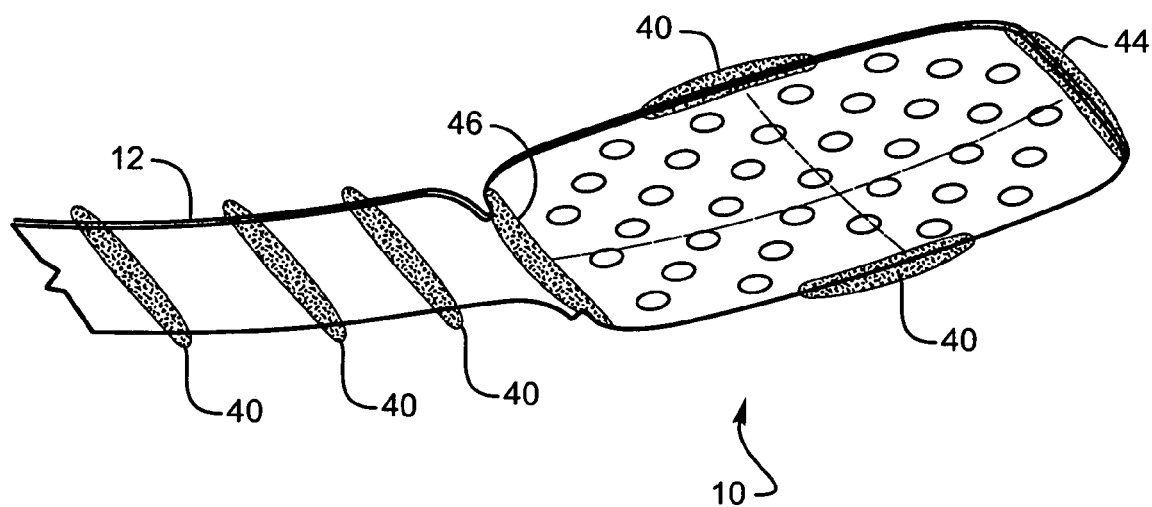
FIG. 4 depicts a perspective view of the invention with ribs to help maintain curvature and prevent retinal damage.

Referring to FIG. 4, the edges of the polymer layers are often sharp. There is a risk that the sharp edges of a flexible circuit will cut into delicate retinal tissue. It is advantageous to add a soft material, such as silicone, to the edges of a flexible circuit electrode array 10 to round the edges and protect the retina. Silicone around the entire edge may make the flexible circuit less flexible. It is advantageous to provide silicone bumpers or ribs to hold the edge of the flexible circuit electrode array 10 away from the retinal tissue. Curvature fits against the retina. The leading edge 44 is most likely to cause damage and is therefore fit with molded silicone bumper. Also, edge 46, where the array lifts off the retina can cause damage and should be fit with a bumper. Any space along the side edges of curvature may cause damage and may be fit with bumpers as well. It is also possible for the flexible circuit cable 12 of the electrode array to contact the retina. It is, therefore, advantageous to add periodic bumpers along the cable 12.

It is also advantageous to create a reverse curve or service loop in the flexible circuit cable 12 of the flexible circuit electrode array 10 to gently lift the flexible circuit cable 12 off the retina and curve it away from the retina, before it pierces the sclera at a scleratomy. It is not necessary to heat curve the service loop as described above, the flexible circuit electrode array 10 can simply be bent or creased upon implantation. This service loop reduces the likelihood of any stress exerted extraocularly from being transmitted to the electrode region and retina. It also provides for accommodation of a range of eye sizes.

With existing technology, it is necessary to place the implanted control electronics outside of the sclera, while a retinal flexible circuit electrode array 10 must be inside the sclera in order to contact the retina. The sclera must be cut through at the pars plana, forming a scleratomy, and the flexible circuit passed through the scleratomy. A flexible circuit is thin but wide. The more electrode wires, the wider the flexible circuit must be. It is difficult to seal a scleratomy over a flexible circuit wide enough to support enough wires for a high resolution array.

Figure 5:
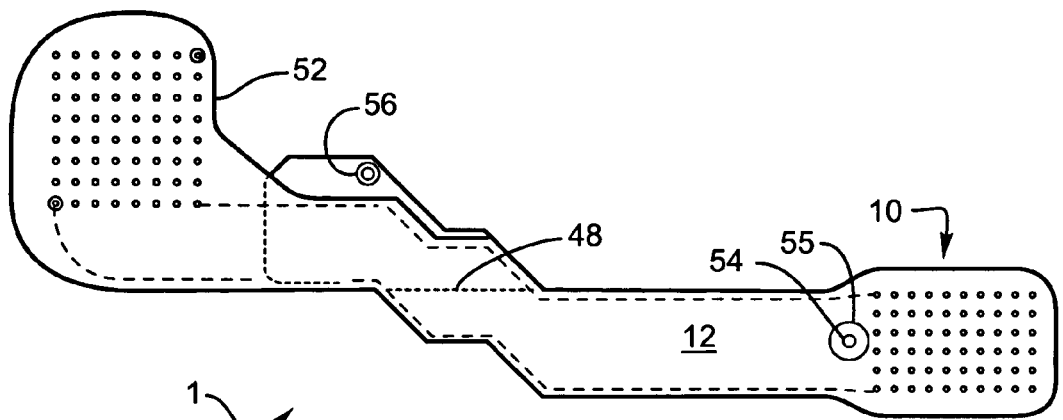
FIG. 5 depicts a top view of a body comprising a flexible circuit electrode array, a flexible circuit cable and a bond pad before it is folded and attached to the implanted portion.

FIG. 5 shows a body 1 containing the flexible circuit electrode array 10, the flexible circuit cable 12 and the interconnection pad 52 prior to folding and attaching the array to the electronics package 14. At one end of the flexible circuit cable 12 is an interconnection pad 52 for connection to the electronics package 14. At the other end of the flexible circuit cable 12 is the flexible circuit electrode array 10. Further, an attachment point 54 is provided near the flexible circuit electrode array 10. A retina tack (not shown) is placed through the attachment point 54 to hold the flexible circuit electrode array 10 to the retina. A stress relief 55 is provided surrounding the attachment point 54. The stress relief 55 may be made of a softer polymer than the flexible circuit, or it may include cutouts or thinning of the polymer to reduce the stress transmitted from the retina tack to the flexible circuit electrode array 10. The flexible circuit cable 12 is formed in a dog leg pattern so than when it is folded at fold 48 it effectively forms a straight flexible circuit cable 12 with a narrower portion at the fold 48 for passing through the scleratomy.

Figure 6:
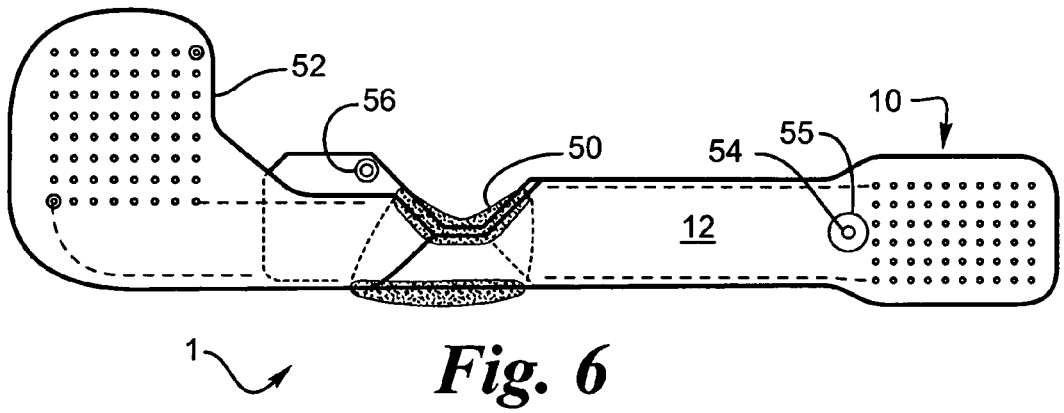
FIG. 6 depicts a top view of a body comprising a flexible circuit electrode array, a flexible circuit cable and a bond pad after it is folded.

FIG. 6 shows the flexible circuit electrode array 10 after the flexible circuit cable 12 is folded at the fold 48 to form a narrowed section. The flexible circuit cable 12 may include a twist or tube shape as well. With a retinal prosthesis as shown in FIG. 1, the interconnection pad 52 for connection to the electronics package 14 and the flexible circuit electrode array 10 are on opposite side of the flexible circuit. This requires patterning, in some manner, both the base polymer layer and the top polymer layer. By folding the flexible circuit cable 12 of the flexible circuit electrode array 10, the openings for the bond pad 52 and the electrodes are on the top polymer layer and only the top polymer layer needs to be patterned.

Also, since the narrowed portion of the flexible circuit cable 12 pierces the sclera, shoulders formed by opposite ends of the narrowed portion help prevent the flexible circuit cable 12 from moving through the sclera. It may be further advantageous to add ribs or bumps of silicone or similar material to the shoulders to further prevent the flexible circuit cable 12 from moving through the sclera.

Further it is advantageous to provide a suture tab 56 in the flexible circuit body near the electronics package 14 to prevent any movement in the electronics package 14 from being transmitted to the flexible circuit electrode array 10. Alternatively, a segment of the flexible circuit cable 12 can be reinforced to permit it to be secured directly with a suture.

Figure 7:
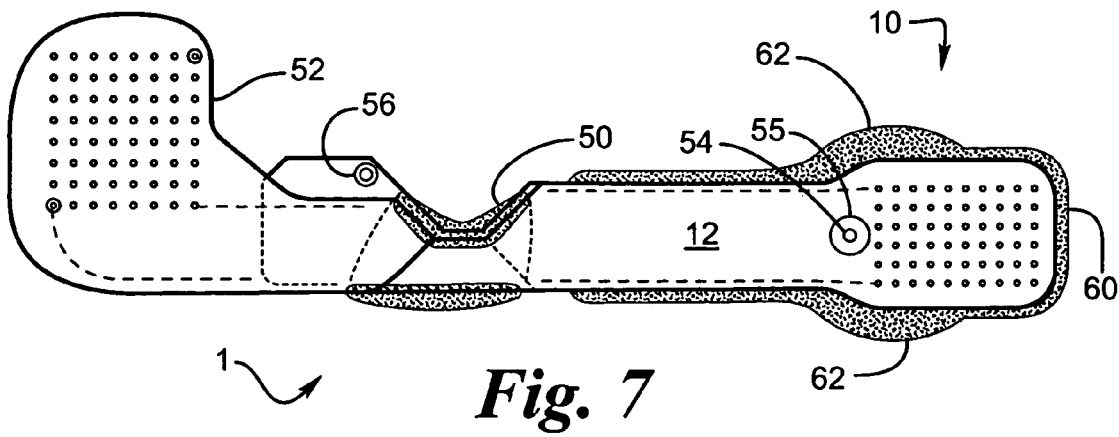
FIG. 7 depicts a top view of a body comprising a flexible circuit electrode array, a flexible circuit cable and a bond pad after it is folded with a protective skirt.

An alternative to the bumpers described in FIG. 4, is a skirt of silicone or other pliable material as shown in FIGS. 5 to 7. A skirt 60 covers the flexible circuit electrode array 10, and extends beyond its edges. It is further advantageous to include windows 62 adjacent to the attachment point 54 to spread any stress of attachment over a larger area of the retina. There are several ways of forming and bonding the skirt 60. The skirt 60 may be directly bonded through surface activation or indirectly bonded using an adhesive as shown in FIG. 7.

Alternatively, a flexible circuit electrode array 10 may be layered using different polymers for each layer. Using too soft of a polymer may allow too much stretch and break the metal traces. Too hard of a polymer may cause damage to delicate neural tissue. Hence a relatively hard polymer, such a polyimide may be used for the bottom layer and a relatively softer polymer such a silicone may be used for the top layer including an integral skirt to protect delicate neural tissue.

Figure 8:
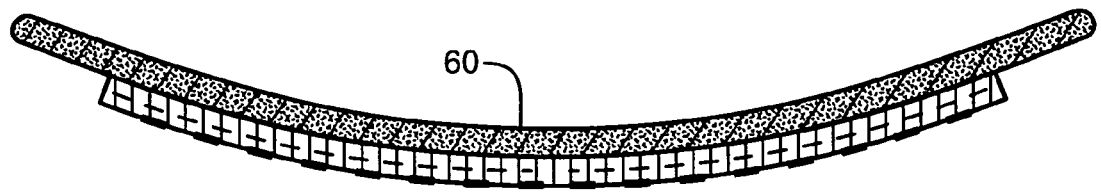
FIG. 8 depicts a cross-sectional view of a flexible circuit array with a protective skirt bonded to the back side of the flexible circuit array.
Figure 9:
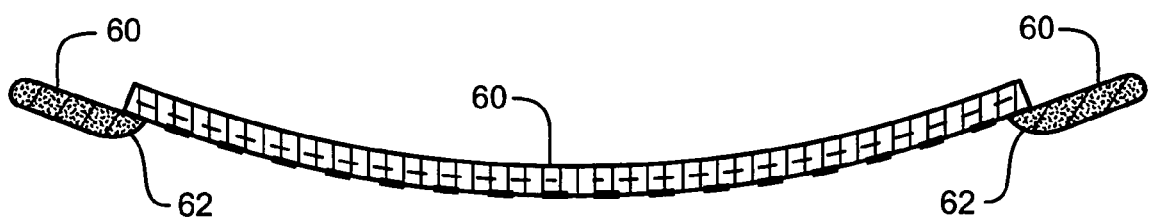
FIG. 9 depicts a cross-sectional view of a flexible circuit array with a protective skirt bonded to the front side of the flexible circuit array.

The simplest solution is to bond the skirt 60 to the back side away from the retina of the flexible circuit electrode array 10 as shown in FIG. 8. While this is the simplest mechanical solution, sharp edges of the flexible circuit electrode array 10 may contact the delicate retina tissue. Bonding the skirt to the front side toward the retina of the flexible circuit electrode array 10, as shown in FIG. 9, will protect the retina from sharp edges of the flexible circuit electrode array 10. However, a window 62 must be cut in the skirt 60 around the electrodes. Further, it is more difficult to reliably bond the skirt 60 to the flexible circuit electrode array 10 with such a small contact area. This method also creates a space between the electrodes and the retina which will reduce efficiency and broaden the electrical field distribution of each electrode. Broadening the electric field distribution will limit the possible resolution of the flexible circuit electrode array 10.

FIG. 8 shows another structure where the skirt 60 is bonded to the back side of the flexible circuit electrode array 10, but curves around any sharp edges of the flexible circuit electrode array 10 to protect the retina. This gives a strong bond and protects the flexible circuit electrode array 10 edges. Because it is bonded to the back side and molded around the edges, rather than bonded to the front side, of the flexible circuit electrode array 10, the portion extending beyond the front side of the flexible circuit electrode array 10 can be much smaller. This limits any additional spacing between the electrodes and the retinal tissue.

Figure 10:
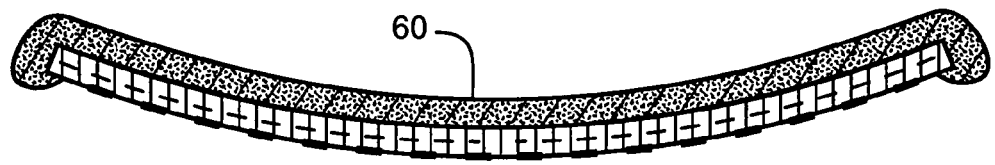
FIG. 10 depicts a cross-sectional view of a flexible circuit array with a protective skirt bonded to the back side of the flexible circuit array and molded around the edges of the flexible circuit array.
Figure 11:
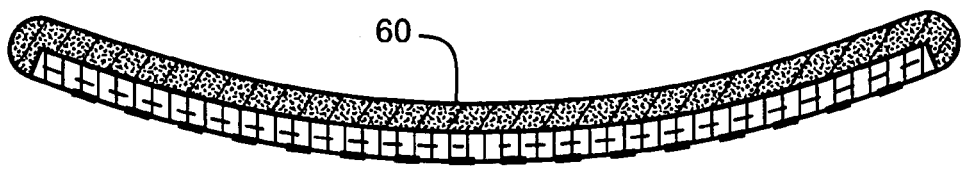
FIG. 11 depicts a cross-sectional view of a flexible circuit array with a protective skirt bonded to the back side of the flexible circuit array and molded around the edges of the flexible circuit array and flush with the front side of the array.

FIG. 9, shows a flexible circuit electrode array 10 similar to FIG. 10, with the skirt 60, flush with the front side of the flexible circuit electrode array 10 rather than extending beyond the front side. While this is more difficult to manufacture, it does not lift the electrodes off the retinal surface as with the array in FIG. 10. It should be noted that FIGS. 8, 10, and 11 show skirt 60 material along the back of the flexible circuit electrode array 10 that is not necessary other than for bonding purposes. If there is sufficient bond with the flexible circuit electrode array 10, it may be advantageous to thin or remove portions of the skirt 60 material for weight reduction.

The electrode of the present invention preferably contains platinum. Platinum can be present in any form in the electrode. The electrode has preferably increased surface area for greater ability to transfer charge and also having sufficient physical and structural strength to withstand physical stress encountered in its intended use. The electrode contains platinum having a fractal configuration so called platinum gray with an increase in surface area of at least 5 times when compared to shiny platinum of the same geometry and also having improved resistance to physical stress when compared to platinum black. Platinum gray is described in US 2003/0192784 "Platinum Electrode and Method for Manufacturing the Same" to David Zhou, the disclosure of which is incorporated herein by reference. The electrodes of the preferred embodiment are too small to display a color without significant magnification. The process of electroplating the surface coating of platinum gray comprising plating at a moderate rate, i.e., at a rate that is faster than the rate necessary to produce shiny platinum and that is less than the rate necessary to produce platinum black.

The flexible circuit electrode array 10 is manufactured in layers. A base layer of polymer is laid down, commonly by some form of chemical vapor deposition, spinning, meniscus coating or casting on a supporting rigid substrate like glass. A layer of metal (preferably platinum), preferably sandwich by layers of another metal for example titanium, is applied to the polymer base layer and patterned to create electrodes and traces for those electrodes. Patterning is commonly done by photolithographic methods. The electrodes may be built up by electroplating or similar method to increase the surface area of the electrode and to allow for some reduction in the electrode over time. Similar plating may also be applied to the bond pads. See FIGS. 5 to 7. A top polymer layer is applied over the metal layer and patterned to leave openings for the electrodes, or openings are created later by means such as laser ablation. It is advantageous to allow an overlap of the top polymer layer over the electrodes to promote better adhesion between the layers, and to avoid increased electrode reduction along their edges. Alternatively, multiple alternating layers of metal and polymer may be applied to obtain more metal traces within a given width.

Figure 12:
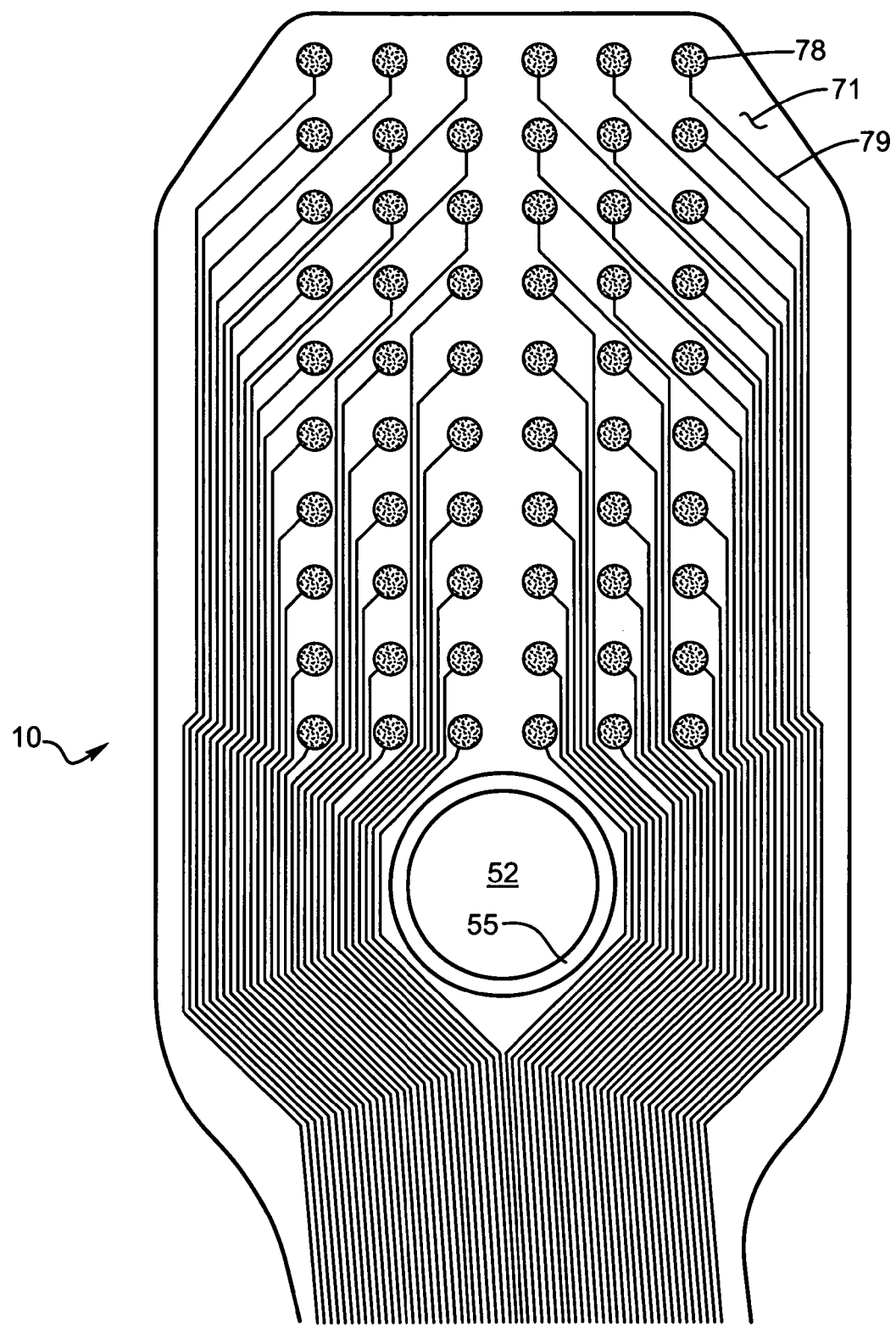
FIG. 12 depicts a top view of the flexible circuit electrode array.

FIG. 12 shows an enlarged top view of the flexible circuit electrode array 10 which is a part of the body 1 as shown for example in FIG. 5. The preferred positions of the electrodes 78 and the preferred wiring by the trace metal 79 both embedded in the polymer 71 are shown in the FIG. 12.

Figure 13:
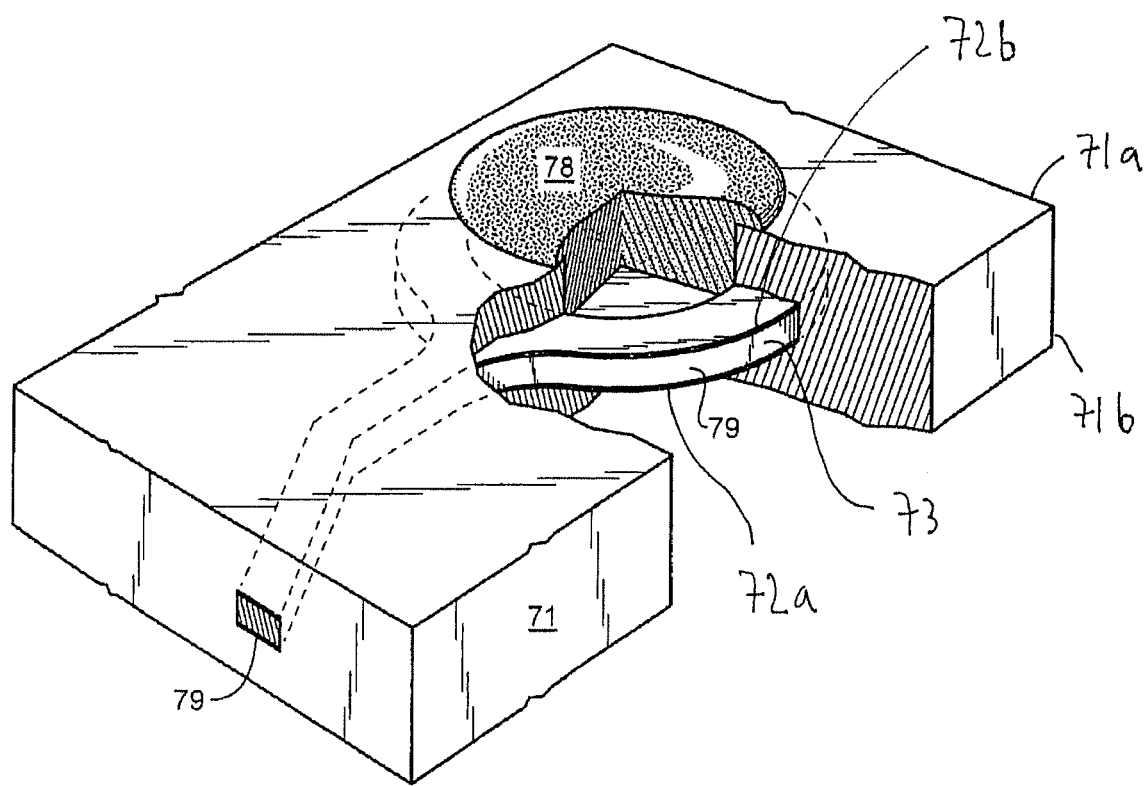
FIG. 13 depicts a perspective view of a part of the flexible circuit electrode array.

FIG. 13 shows a three dimensional view of a part of the flexible circuit electrode array 10. It shows one electrode 78 which has a contact with the trace metal 79. It also shows that the trace metal 79 overlaps the electrode 78 and the electrode 78 overlaps the via in the polymer 71. The FIG. 13 further shows the adhesion of the polymer 71 with the trace metal 79 and the electrode 78 which results in a very high effective insulation of the trace metal 79 and the electrode 78. FIG. 13 shows also that the trace metal 79 is preferably composed of platinum intermediate conducting layer 73 covered on the lower and upper side preferably with a thin titanium top conducting layer 72*a* and thin titanium base conducting layer 72*b*. FIG. 13 finally shows that the first applied base polymer 71*a* and the subsequently applied top polymer layer 71*b* form a single polymer layer 71.

Figure 14:
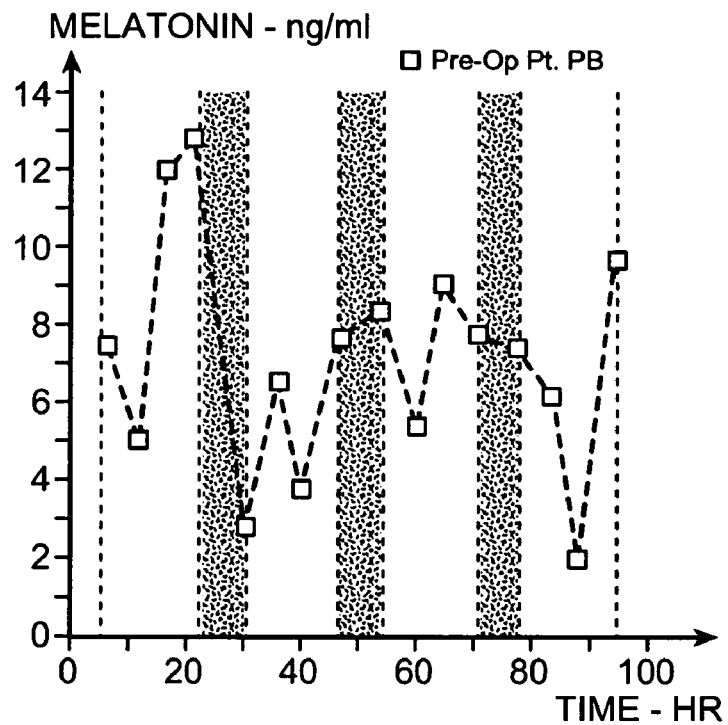
FIG. 14 is a graph of experimental data showing patient PB preoperative.

FIG. 14 shows melatonin levels for a first patient, PB, preoperative. The vertical axis is melatonin levels as measured with a mouth swab every four hours. The horizontal axis is time, where the shaded portions are normal night time hours, over a four day period. There is no significant increase in melatonin levels at night. In fact melatonin decreased on average during the night time periods.

Figure 15:
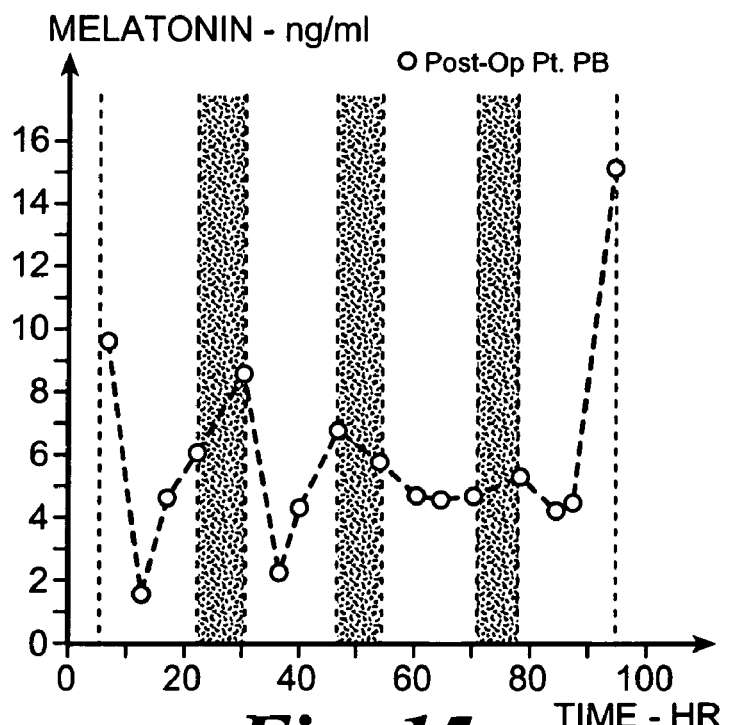
FIG. 15 is a graph of experimental data showing patient PB postoperative.

FIG. 15 shows the same patient, as in FIG. 14, using the retinal prosthesis of the current invention. Melatonin levels increased, on average, during the night time hours.

Figure 16:
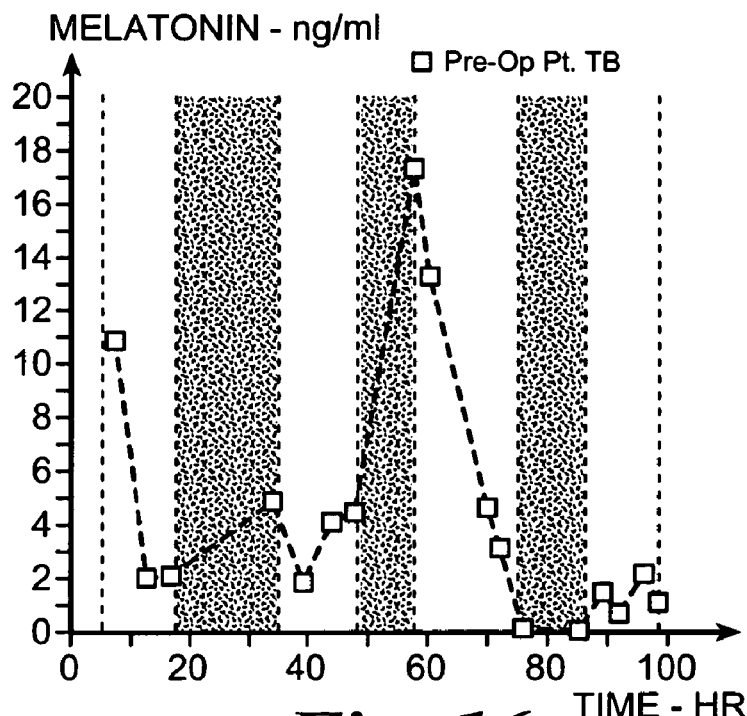
FIG. 16 is a graph of experimental data showing patient TB preoperative.

FIG. 16 shows a second patient TB, preoperative with, on average increased melatonin levels at night, but inconsistent results.

Figure 17:
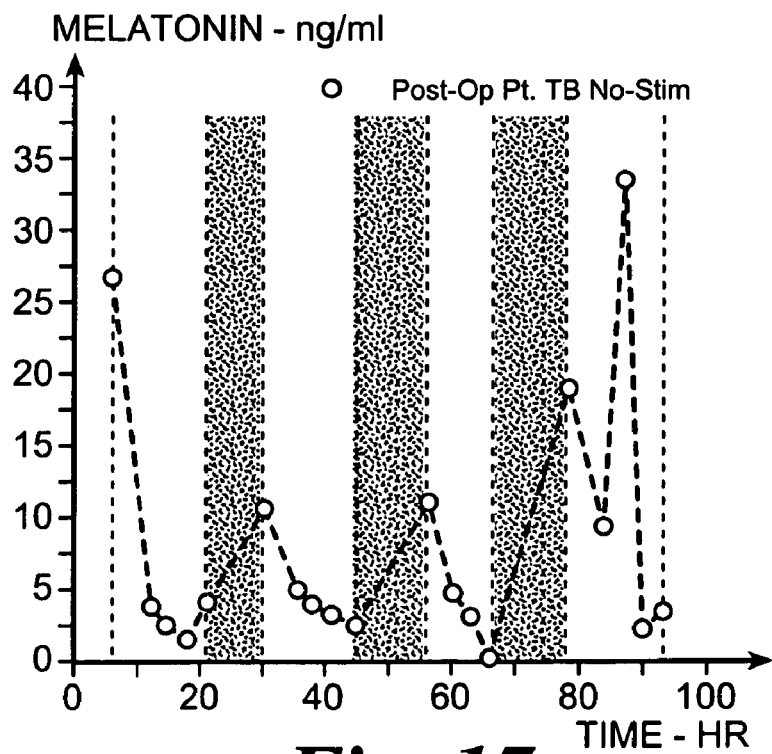
FIG. 17 is a graph of experimental data showing patient TB postoperative.

FIG. 17 shows the second patent, as in FIG. 16, using the retinal prosthesis of the current invention. Melatonin level increase significantly, and consistently.

An alternative embodiment of the present invention can be used when surgery is not desired due to health or surgical apprehension. An external electrode can be attached to the cornea in a form similar to a contact lens, or mounted to the inside of a pair of dark glasses. While such external electrodes can not created formed vision, they can create artificial light during the daytime and be turned, or removed, to create artificial darkness at night. Such an electrode would make it possible to control and improve the melatonin production for patients who are not necessarily vision impaired or blind.

The present invention will be further illustrated by the following examples, but it is to be understood that the invention is not meant to be limited to the details described herein.

EXAMPLES

In the present example the inventors modulate the above system artificially through retinal prostheses in two patients with retinitis pigmentosa.

Two patients TB and PB who had retinitis pigmentosa and no light perception (NLP) for five (5) and twenty (20) years were examined. The two patients and a normal control had a multiple saliva samples taken over the course of four (4) days and assayed for melatonin. The two patients then had surgical implantation of the retinal prosthetic implant. The prosthesis was electrically stimulated in one subject. The patients and the normal control were then evaluated with several saliva sampling over the course of four (4) days.

Melatonin concentrations in saliva samples were measured using a commercially availably melatonin ELISA assay (n=83) from ALPCO Diagnostic, Windham, N.H. 03087. Concentrations were calculated by fitting to a standard logistic equation. A cosinor analysis was performed on the data set using commercially available software from Expert Soft Tech.

The normal control showed typical circadian levels of melatonin with morning peaks and day time lows with a period of 1430 minutes (24 hours=1440 minutes) an about 62% rhythm.

Both patients with advanced retinitis pigmentosa showed decreased periodicity of melatonin levels preoperatively. Patient PB exhibited a period of 925 minutes with 21% rhythm. While the period could not be calculated for patient TB, he displayed 39% rhythm.

Patient PB did not show preoperative significant increase in melatonin levels at night. In fact melatonin decreased on average during the night time periods as shown in the shaded normal night time hours over four day period in FIG. 14.

Patient TB showed preoperative on average increased melatonin levels at night, but inconsistent results as shown in the shaded normal night time hours over four day period in FIG. 16.

After surgical implantation of the retinal prosthetic, both patients PB and TB with or without prosthetic stimulation showed doubling of the percent rhythm and a normalization of their periods 1360 and 1430 minutes as would be expected from a normal circadian rhythm.

Patient PB after using the retinal prosthesis of the current invention showed significant increase in melatonin levels at night as shown in the shaded normal night time hours over four day period in FIG. 15.

Patient TB showed after using the retinal prosthesis of the current invention a significant consistent increase in melatonin levels at night as shown in the shaded normal night time hours over four day period in FIG. 17.

The data suggest that entrainment of circadian rhythms is possible in patients with retinitis pigmentosa, and that the retinohypothalamic pathway that modulates circadian rhythms is intact.

The data additionally suggest that it is possible to recover entrainment of the circadian rhythm with implantation surgery.

Accordingly, an improved method making a visual prosthesis and improved method of stimulating neural tissue has been shown. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What we claim is:

1. A flexible circuit electrode array adapted to be used with a visual prosthesis, comprising:
   a) an insulating polymer layer comprising a top polymer portion and a bottom polymer portion;
   b) at least one trace containing a base conducting layer, an intermediate conducting layer and a top conducting layer, embedded in said insulating polymer layer between said top polymer portion and said bottom polymer portion; and
   c) at least one electrode connected to said at least one trace through a via in said top polymer portion of said insulating polymer layer, wherein said electrode includes a first electrode portion contacting said trace through said via and a second electrode portion overlapping said trace above said top polymer portion, and wherein a region of said top polymer portion is defined between said trace and said second electrode portion, wherein the first electrode portion is a central electrode portion contacting a corresponding central portion of the trace and the second electrode portion is a peripheral annular-shaped portion overlapping a corresponding peripheral annular-shaped of the trace above said top polymer portion.

2. The flexible circuit electrode array of claim 1 wherein said insulating polymer layer contains polyfluorocarbons, polyethylene, polypropylene, silicone, polyamide, polyimide, liquid crystal polymer, poly-paraxylylene, polyaryletherketone and/or derivatives and/or mixtures thereof.

3. The flexible circuit electrode array of claim 1 wherein said intermediate conducting layer contains platinum, tantalum, iridium, palladium, rhodium, rhenium, gold, chrome, molybdenum, or carbon, or an alloy thereof or a combination of two or more alloys or metal layers thereof.

4. The flexible circuit electrode array of claim 1, wherein the base conducting layer and the top conducting layers of the trace are made of titanium, and the intermediate conducting layer is made of platinum whereby said trace forms a titanium/platinum/titanium film stack.

5. The electrode array of claim 1 wherein the at least one electrode comprises a surface coating, said surface coating having at least 5 times the surface area of that for the corresponding surface area resulting from the basic geometric shape of the electrode.

6. The flexible circuit electrode array of claim 1 wherein the at least one electrode comprises a surface coating, said surface coating being biocompatible.

7. The flexible circuit electrode array of claim 1 wherein the at least one electrode comprises a surface coating, said surface coating having a surface area of less than 500 times the corresponding surface area resulting from the basic geometric shape.

8. The flexible circuit electrode array of claim 1 wherein the at least one electrode comprises a surface coating, said surface coating comprising platinum having a fractal configuration, titanium nitride, iridium oxide, or mixtures thereof.

9. The flexible circuit electrode array of claim 1, wherein said top polymer portion and said bottom polymer portion are made of different polymers.

10. The flexible circuit electrode array of claim 9, wherein said top polymer portion is made of a polymer softer than the polymer of said bottom polymer portion.

11. The flexible circuit electrode array of claim 10, wherein said bottom polymer portion is made of polyimide and said top polymer portion is made of silicone.

12. The flexible circuit electrode array of claim 1 wherein the trace separates the electrode from the bottom polymer portion.

13. The flexible circuit electrode array of claim 1, wherein the electrode protrudes from the top polymer portion.

14. The flexible circuit electrode array according to claim 1, wherein the electrode is thicker than the trace.

15. The flexible circuit electrode array according to claim 1, wherein the trace is wider at the electrode than it is along the rest of its length.

16. The flexible circuit electrode array according to claim 1, wherein the second electrode portion defines a circle coaxial to the via around the central electrode portion and the peripheral annular-shaped portion of the trace defines a circle coaxial to the via around the central portion of the trace.

17. A flexible circuit electrode array adapted to be used with a visual prosthesis, comprising:
   a) an insulating polymer layer comprising a top polymer portion and a bottom polymer portion;
   b) at least one trace containing a base conducting layer, an intermediate conducting layer and a top conducting layer, embedded in said insulating polymer layer between said top polymer portion and said bottom polymer portion; and
   c) at least one electrode connected to said at least one trace through a via in said top polymer portion of said insulating polymer layer, wherein said electrode includes a first electrode portion contacting said trace through said via and a second electrode portion overlapping said trace above said top polymer portion, and wherein a region of said top polymer portion is defined between said trace and said second electrode portion, wherein the trace includes a plate-shaped trace portion, and wherein the first electrode portion is a central portion contacting a central portion of the plate-shaped trace portion, and the second electrode portion is a perimeter portion overlapping a perimeter portion of the plate-shaped trace portion above said top polymer portion, the perimeter portion of the plate-shaped trace portion defining a closed line portion around the central portion of the plate-shaped trace portion.

18. The flexible circuit electrode array according to claim 17, wherein the perimeter portion of the plate-shaped trace portion is a ring-shaped or annular-shaped portion.

* * * * *